US009594740B1

(12) United States Patent
Reddy

(10) Patent No.: US 9,594,740 B1
(45) Date of Patent: Mar. 14, 2017

(54) FORMS PROCESSING SYSTEM

(71) Applicant: INTERNATIONAL BUSINESS MACHINES CORPORATION, Armonk, NY (US)

(72) Inventor: Dandala Vinod Reddy, Apex, NC (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/188,087

(22) Filed: Jun. 21, 2016

(51) Int. Cl.
*G06F 17/20* (2006.01)
*G06F 17/24* (2006.01)
*G06F 17/27* (2006.01)
*G06F 17/22* (2006.01)

(52) U.S. Cl.
CPC .......... *G06F 17/243* (2013.01); *G06F 17/248* (2013.01); *G06F 17/273* (2013.01); *G06F 17/2735* (2013.01); *G06F 17/2264* (2013.01)

(58) Field of Classification Search
CPC .. G06F 17/243; G06F 17/248; G06F 17/2735; G06F 17/273; G06F 17/2264
See application file for complete search history.

(56) References Cited

U.S. PATENT DOCUMENTS

| 8,315,484 | B2 | 11/2012 | Meyer et al. | |
|---|---|---|---|---|
| 8,792,141 | B2* | 7/2014 | Moore | G06K 9/00449 358/1.1 |
| 8,805,803 | B2 | 8/2014 | Simske et al. | |
| 2002/0141660 | A1* | 10/2002 | Bellavita | G06K 9/2054 382/309 |
| 2003/0138144 | A1* | 7/2003 | Lynggaard | G06K 9/723 382/181 |
| 2005/0196074 | A1* | 9/2005 | Deere | G06K 9/2054 382/305 |
| 2006/0007189 | A1* | 1/2006 | Gaines, III | G06F 17/243 345/179 |

(Continued)

OTHER PUBLICATIONS

Bishop, Camily, "OCR? ICR? IWR? OMG! Get the Most from Your Scanned Text", Jan. 29, 2015, Crowley, 5 pages.*

(Continued)

*Primary Examiner* — William Bashore
*Assistant Examiner* — David Faber
(74) *Attorney, Agent, or Firm* — Weitzman Law Offices LLC

(57) ABSTRACT

A forms processing system involves at least one processor, storage, an intelligent character, and/or intelligent word, recognition program, multiple selectable forms-scanning templates, an intelligent analysis module, and first and second field-specific dictionaries. The intelligent analysis module will, when analysis of particular content in a first or second field indicates that the particular content may be misspelled or improper or is absent from the respective field-specific dictionary, will attempt to identify a closest fit between the particular content and contents of the respective field-specific dictionary and either: a) automatically replace the particular content with an entry from the respective field-specific dictionary corresponding to the closest fit when a discrepancy is not likely, or b) if there is no closest fit or the particular content is absent, provide an error indication to an operator for operator correction, and store the correction as a new entry within the respective field-specific dictionary.

1 Claim, 3 Drawing Sheets

(56) References Cited

U.S. PATENT DOCUMENTS

| | | | |
|---|---|---|---|
| 2007/0168382 A1* | 7/2007 | Tillberg | G06F 17/30253 |
| 2008/0181501 A1* | 7/2008 | Faraboschi | G06F 3/03545 |
| | | | 382/179 |
| 2010/0011280 A1* | 1/2010 | Cheeniyil | G06F 17/243 |
| | | | 715/223 |
| 2014/0089302 A1 | 3/2014 | Lapir et al. | |
| 2014/0180670 A1* | 6/2014 | Osipova | G06F 17/276 |
| | | | 704/3 |
| 2015/0269862 A1* | 9/2015 | Gross | G09B 7/02 |
| | | | 434/162 |
| 2015/0278593 A1* | 10/2015 | Panferov | G06K 9/00483 |
| | | | 382/182 |

OTHER PUBLICATIONS

Riley, Chris, What's the difference between ICR and OCR technologies?, Sep. 18, 2011, 9 pages.*

Pay, Brittany, "The Difference Between OCR and ICR and Why It Matters for Organizations Using DMS", Dec. 8, 2015, 5 pages.*

Cvision, "ICR and OCR Technology for Forms", civsiontech.com, Mar. 2, 2016, 1 page.*

* cited by examiner

FORMS PROCESSING SYSTEM

FIELD OF THE INVENTION

This disclosure relates generally to computers and, more particularly, to forms processing systems.

BACKGROUND

Forms processing is used to recognize and extract text as per defined zones in a form. This is particularly difficult where the text extracted from a page consists of hand-printed or cursively written data. In some cases, using a dictionary, the extracted text is sufficiently clear that it can be recognized as erroneous and corrected automatically, for example, the written word "audible" being extracted and recognized as "audi6le" (i.e., the lowercase "b" is recognized as the number "6") can be located in a dictionary and corrected because English language words don't have numbers within them, but, in many cases, that is not possible, for example, text containing reference to "60 ml" could be recognized as being ambiguous or anomalous because it is not clear whether the extracted text data is properly "boml" (or a misspelling of some variant) or an intended (but partly undecipherable) number, e.g., "60?1" so that text data must be manually verified by an operator as part of the scanning process, or it will be sent with all such ambiguities and/or anomalies, to a content management repository using a follow-on process to flag such issues for manual review and verification. Such efforts are labor intensive and, consequently, costly.

Thus, there is an ongoing technological problem involving forms processing involving forms containing handwriting.

SUMMARY

One aspect of this disclosure involves a forms processing system comprising: i) at least one processor; ii) non-transitory storage coupled to the at least one processor; iii) at least one of an intelligent character recognition (ICR) or intelligent word recognition (IWR) program stored in the storage and executable by the at least one processor; iv) multiple selectable forms-scanning templates, stored in the storage and selectable for use with the at least one ICR or IWR program based upon an analysis of an individual form to be scanned for text conversion using the at least one ICR or IWR program, each of the multiple forms-scanning templates having multiple fields, defining specific content areas of filled-in forms to be scanned for graphic content that is to be recognized and converted into text content using the at least one ICR or IWR program; v) an intelligent analysis module, stored within the storage and executable by the at least one processor which, when executed, will load field-specific dictionaries, based upon fields within a particular template, and analyze converted text content obtained from within the recognized specific content areas of a filled-in form for misspellings or improper entries using the field-specific dictionaries before saving the converted text content into the storage; vi) a first field-specific dictionary, stored in the storage and linked to one of the fields of one of the forms-scanning templates, the first field-specific dictionary being used by the intelligent analysis module to check for misspelling or improper entry within first converted text content located within a first content area of a scanned filled-in form document, the first content area corresponding to the one of the fields, and having been converted by the at least one ICR or IWR program; vii) a second field-specific dictionary, different from the first, stored in the storage, and linked to an other of the fields of the one forms-scanning template, the second field-specific dictionary being used by the intelligent analysis module to check for misspelling or improper entry within second converted text content located within a second content area of the scanned filled-in form document, the second content area corresponding to the other of the fields and having been converted by the at least one ICR or IWR program. Wherein, the intelligent analysis module will, when analysis of particular content in one of the first field or the second field indicates that the particular content may be misspelled or improper or is absent from the respective first or second field-specific dictionary linked to the first field or the second field, and based upon which of the first or second fields contains the particular content that is misspelled or improper, will attempt to identify a closest fit between the particular content and contents of the respective first or second field-specific dictionary and either: a) automatically replace the particular content with an entry from the respective first or second field-specific dictionary corresponding to the closest fit when a discrepancy between the particular content and the entry is not likely, or b) if there is no closest fit, or the particular content is absent, provide an indication of an error to an operator, via a user interface, and allow the operator to provide a correction for the particular content. Wherein, if the correction provided by the operator does not correspond to content within the respective first or second field-specific dictionary, the intelligent analysis module will automatically store the correction as a new entry within the respective first or second field-specific dictionary in the storage for use by the intelligent analysis module in a subsequent analysis of new content from a new scanned form document involving the respective first or second field-specific dictionary to which the correction was added.

Advantageously, through use of a system as described herein, processing of forms containing handwriting can be expedited and the manual labor associated with such processing can be reduced.

The foregoing and following outlines rather generally the features and technical advantages of one or more embodiments of this disclosure in order that the following detailed description may be better understood. Additional features and advantages of this disclosure will be described hereinafter, which may form the subject of the claims of this application.

BRIEF DESCRIPTION OF THE DRAWINGS

This disclosure is further described in the detailed description that follows, with reference to the drawings, in which.

DETAILED DESCRIPTION

This disclosure provides a technical solution to address the aforementioned problems inherent with forms processing involving handwriting This technical solution is an improvement to the forms processing field in general and provides a specific improvement to the computer technology used in processing of forms containing handwriting.

Figure 1:
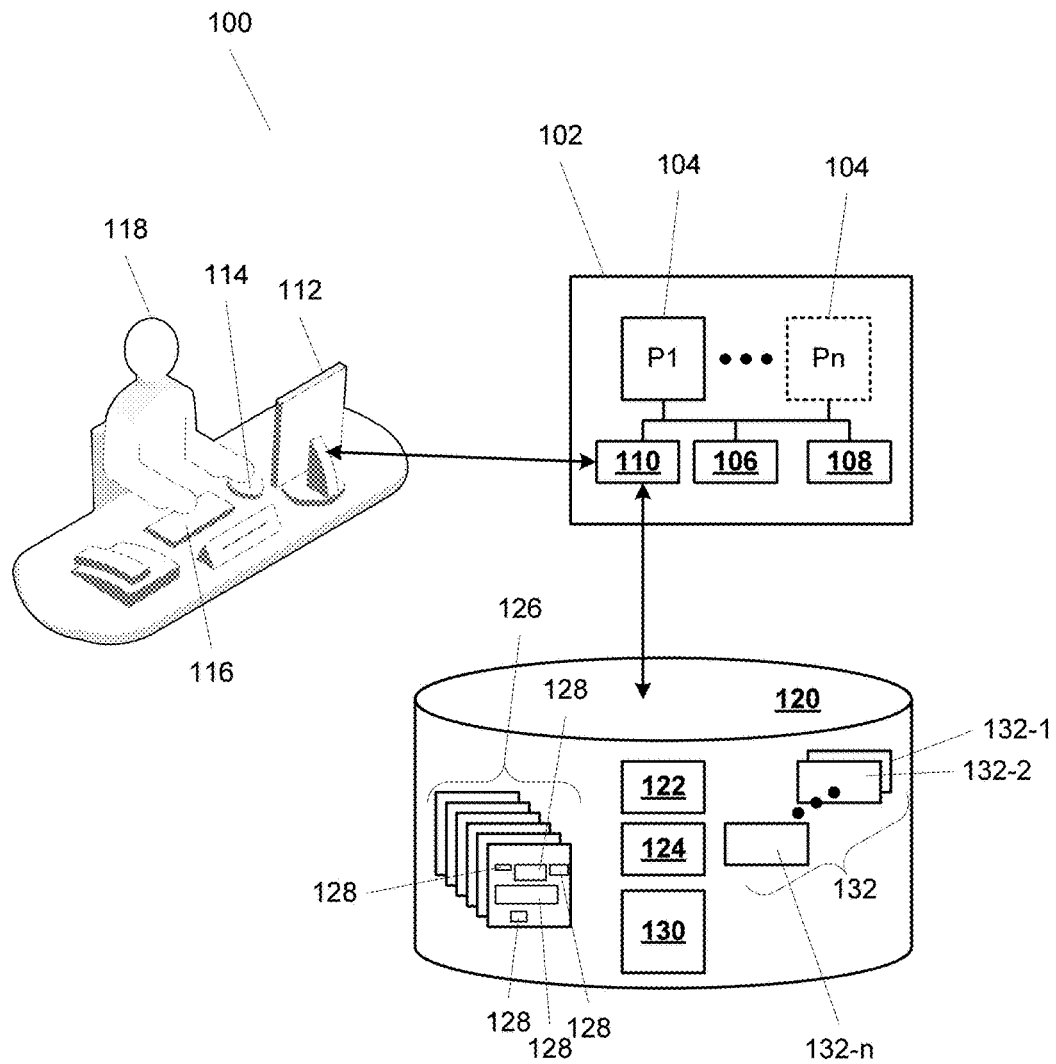
FIG. 1 illustrates, in simplified form, an overview of a system incorporating form processing as described herein.

FIG. 1 illustrates, in simplified form, an overview of a system 100 incorporating form processing as described herein.

As shown, the system includes a computer 102, which, in its simplest form may be a conventional computer, or, in more complex implementations, may be, for example, one or more servers or even a minicomputer or mainframe computer. The computer 102 includes at least one processor 104, and potentially more processors. As used herein, it is to be understood that the term "processor" is intended to encompass all kinds of processors, including single core and multi-core microprocessors. The computer also includes conventional aspects like RAM 106, ROM 108 and I/O 110, via which the computer 102 can output information to a display 112 and receive input, for example, from a device like a mouse 114 or keyboard 116, from a user 118.

The system 100 also includes storage, coupled to the processor(s) 104 so that the processor can read from and write to that storage 120. Note here that, unless specifically stated otherwise, all references to "storage" are intended to mean one or more devices that can be accessed by a processor and stores data, data-containing structures, and program instructions in a non-transitory manner, for example, such as non-transient solid state memory, a magnetic hard drive, a CD or DVD, a tape drive, or an analogous or equivalent storage medium type would.

The storage 120 has stored within it at least one of an intelligent character recognition (ICR) program 122 and/or an intelligent word recognition (IWR) program 124, as well as multiple forms-scanning templates 126 that each have multiple fields 128 that define specific content areas where graphic content (e.g., handwriting) should be in a particular corresponding scanned form and is to be recognized and converted into text content, and an intelligent analysis module 130 and multiple field-specific dictionaries 132 (132-1, 132-2, . . . , 132-n).

The intelligent character recognition (ICR) program 122 and/or an intelligent word recognition (IWR) program 124 are software programs, executable by the processor(s) 104, that are designed to respectively recognize handwritten characters or whole words/phrases, for example, using technology described in U.S. Pat. No. 5,392,363, U.S. Pat. No. 5,644,652, U.S. Pat. No. 5,862,251, U.S. Pat. No. 6,256,410, U.S. Pat. No. 6,320,985, U.S. Pat. No. 6,370,269 (all incorporated herein by reference in their entirety), or other suitable known written character, word or phrase recognition technology.

The forms-scanning templates 126 are data structures, that can be selected by the ICR program 122 or IWR program 124 from the storage 120, that each correspond to a particular form that can be scanned and converted by the system. As noted above, each individual forms-scanning template 126 has multiple fields 128 that define specific areas where a given form should have filled in graphic content (e.g., handwriting) and it is the content within those specific areas that are to be recognized and converted into text by the ICR program 122 or IWR program 124. Thus, once a filled-in form is scanned, the forms-scanning template 126 for that form will limit what parts of the filled-in form need to be recognized and converted.

The intelligent analysis module 130 is a software program (or, depending upon the particular implementation, part of a larger software program), stored in the storage 120 and executable by the processor(s) 104 that is the "brains" of the system. The intelligent analysis module 130 compares a scanned document to the multiple forms-scanning templates 126 and selects an appropriately corresponding forms-scanning template. In addition, once a forms-scanning template has been selected, the intelligent analysis module 130, will load field-specific dictionaries based upon the fields in that template and, using each field-specific dictionary, analyze the converted text in the corresponding field for any misspelling(s) or improper entr(y/ies) before saving that converted text content in the storage associated with that filled-in form.

Figure 2:
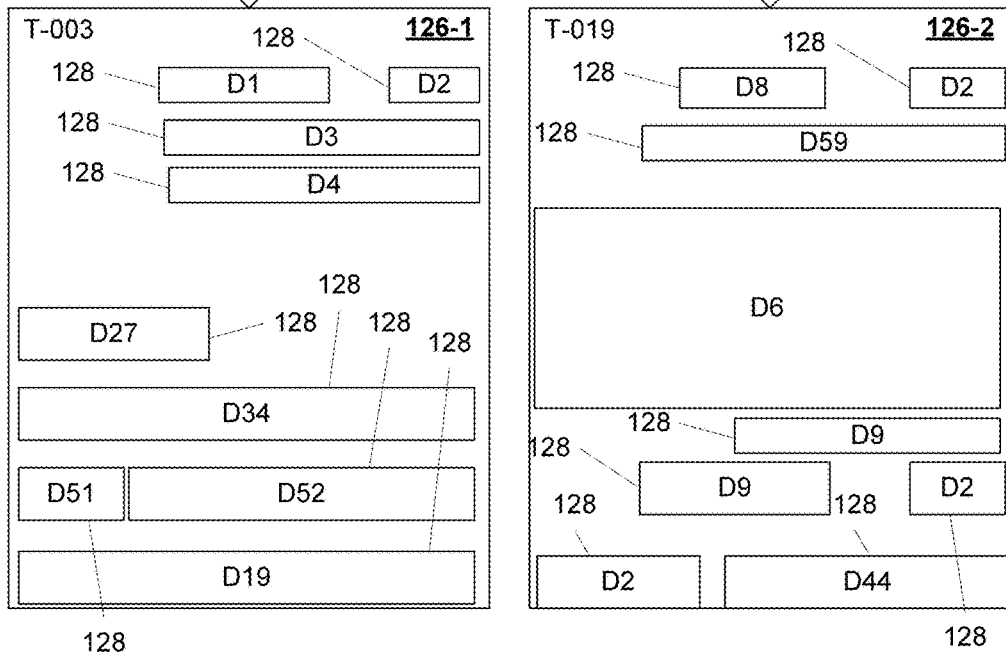
FIG. 2 illustrates, in simplified form, two simplified examples of forms and associated forms-scanning templates.

FIG. 2 illustrates, in simplified form, two simplified examples of forms and associated forms-scanning templates. As shown in FIG. 2, there are two forms 202, 204 that can be filled in by someone, a "Medical Reporting Form" 202 and a "Purchase Request Form" 204. Each of the forms have different information that can be handwritten in when the form is being filled out. Each of those forms has, stored within the storage 120 of the system 100, a corresponding specific template 126-1, 126-2.

As described above, when a forms processing system 100 as described herein receives a scan of a filled-in form, for example, one that corresponds to the "Medical Reporting Form" 202, the intelligent analysis module 130 will examine that form and search through the stored templates 126 to identify the correct template for that form, in this example, the template 126-1 (labeled in FIG. 2 with "T-003") which contains multiple fields 128 that each identify a corresponding field-specific dictionary 132 (D1, D2, D3, D4, D19, D27, D34, D51, D52) which are specific to the potential individual content for those fields 128. In contrast, if the same forms processing system 100 received a scan of a different filled-in form, for example, one that corresponds to the "Purchase Request Form" 204, intelligent analysis module 130 would examine that form and identify a different template, template 126-2 (labeled in FIG. 2 with "T-019"). That template has multiple fields 128 as well, but those fields each identify different field specific dictionaries 132 (D2, D6, D8, D9, D44, D59) specific to those fields. Note here that, depending upon the particular form and template, a given dictionary 132-1 may, however, be used across multiple forms 202, 204, for example, because the templates 126-1, 126-2 each have a "date" field 128 (i.e., in this example, dictionary "D2" contains dates), and/or the same dictionary 132-2 may be used for multiple fields within a form 126-2 (e.g., dictionary "D9" contains people's names) because its contents, for example, name of an employee, could appear in any of those fields.

As alluded to above, each field-specific dictionary 132-1, 132-2, . . . , 132-n is linked to at least one of the fields 128 of one of the forms-scanning templates 126.

On a per-field basis, the intelligent analysis module 130 will use the associated field-specific dictionary 132 to analyze converted content for that particular field 128 to identify any misspelling or improper content within that field 128. Advantageously, by using this approach, introduction of errors can be reduced because the potential corrections are limited to those within the particular dictionary germane to the expected content (for example, medications), thereby avoiding flagging every potential error for operator review or introducing/missing errors through use of a generic dictionary (e.g., correcting a misspelled/mis-converted "pencilin into "pencil" or "pencil in", or missing an improperly input/mis-converted (but proper spelling) "6 inch bell", "6 inch belt" that should be "6 inch bolt").

Thus, in operation, when the intelligent analysis module 130 analyzes the particular content within a given field 128, using the field-specific dictionary 132 linked to that field 128, and that analysis indicates that some particular content may be misspelled or improper, or that content is absent from that field-specific dictionary 132, intelligent analysis module 130 can take appropriate action. In the case where the particular content may be misspelled or improper, the intelligent analysis module 130 will attempt to identify the closest fit correction as between the particular content and the contents of that field-specific dictionary. Depending upon the particular implementation and situation, this may involve, in the simplest case, simply automatically replacing the particular content with an entry from that dictionary 132 that it identifies as the closest fit (for example, "penicillin" for "pencilin" or "1 ml" for "hnl") when a discrepancy between the two is unlikely. In a more complex case, this may involve employing further logic, in conjunction with content in one or more other fields, to ascertain what is proper. For example, if the "description" field contains a particular misspelled/improper converted word (e.g., "bult" which could be "bell", "belt", "bolt", "ball", etc.), the intelligent analysis module 130 can look at, for example, a "SKU" or "part number" field and/or "unit price" field to identify which correction is proper.

Typically, only, in a case where, the intelligent analysis module 130 cannot identify a closest fit for particular content, and after otherwise completing analysis of the entire scanned document, will the intelligent analysis module 130 flag this circumstance as a problem and provide an error indication to an operator, via an appropriate user interface (e.g., a screen 112 display, print out, error message in a log, etc.) so that the operator 118 can review and provide an appropriate correction. Advantageously, as a result, the system 100 flag the specific error to the operator 118 and the operator can presume that every thing else is correct.

Presume, for example, that the intelligent analysis module 130 of the system 100 cannot ascertain a correct entry, by way of example, assume that a new insurance code for a particular procedure or diagnosis has recently been added or changed, such that it does not appear in the field-specific dictionary for that field, or the field has been left blank because the person filling in the form did not know the new/changed code at the time. As a result, that form's field would be flagged for operator 118 intervention. Advantageously, all operator corrections/modifications are handled by the intelligent analysis module 130 so that, when an operator 118 makes some change or entry, the intelligent analysis module 130 will compare the operator's 118 entry with the contents of the field-specific dictionary linked to that field.

If the operator's 118 entry corresponds with content already in that field-specific dictionary, the intelligent analysis module 130 can create an association between that entry and other field-specific dictionary content within the form so that future analysis can have the benefit of that correction and avoid requiring operator intervention. Thus, for example, if multiple forms suffer the same situation of the missing code, and a correction is made by an operator 118 the first time it comes up in a form, based upon the associations with one or more other field contents, the intelligent analysis module 130 can learn to automatically insert the proper code.

Likewise, if the operator's correction does not correspond with content already in that dictionary, the intelligent analysis module 130 will automatically store the new entry by the operator in the field-specific dictionary linked to that field for use by the intelligent analysis module 130 thereafter in connection with analysis of future filled-in forms that involve that field-specific dictionary.

Figure 3:
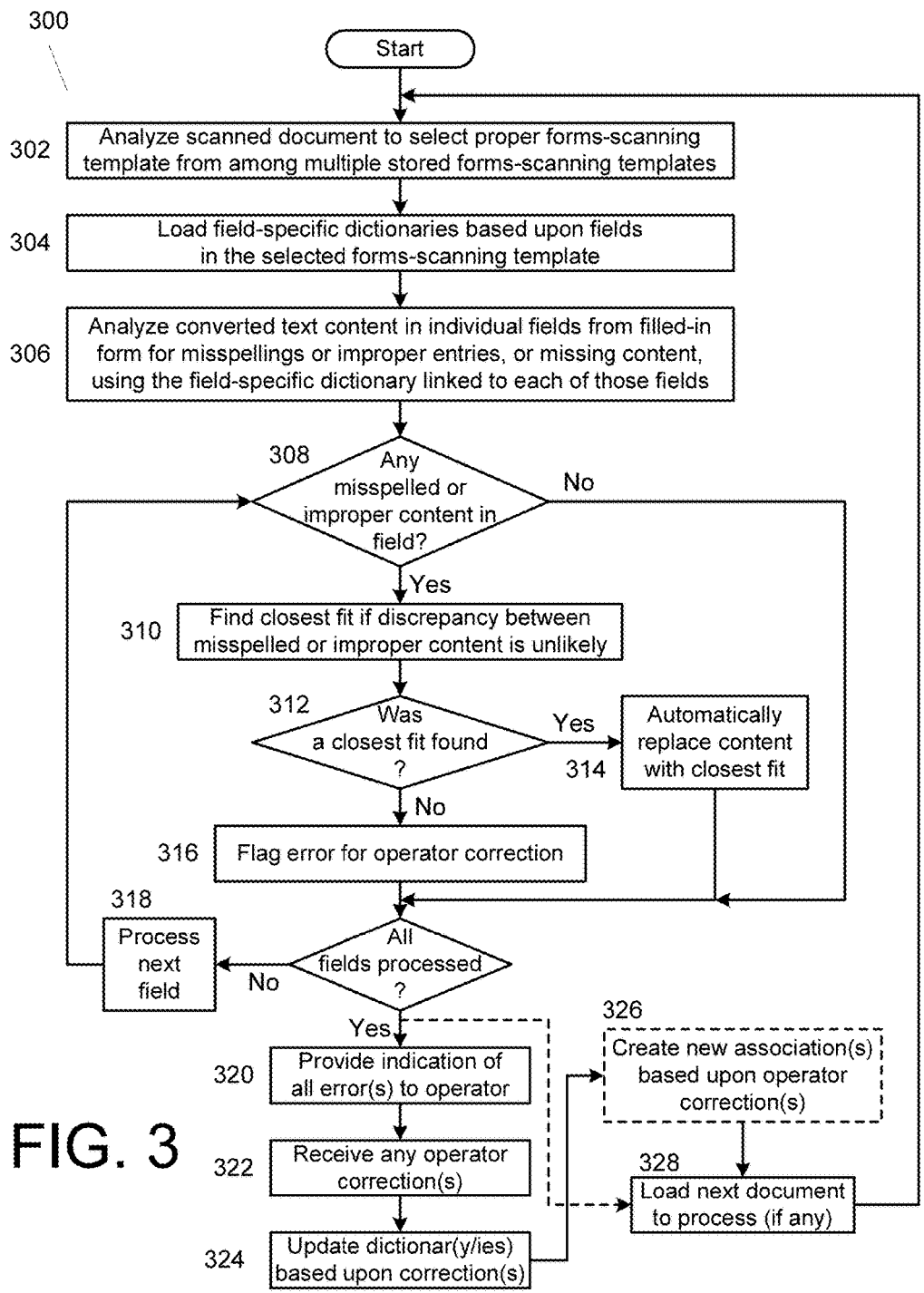
FIG. 3 is a simplified flowchart for an example process performed by one example of an intelligent analysis module as described herein.

FIG. 3 is a simplified flowchart 300 for an example process performed by one example of an intelligent analysis module 130 as described herein.

The process begins with the intelligent analysis module 130 being executed by the processor(s) 104 and analyzing a scanned document to select the proper forms-scanning document from among the multiple forms-scanning templates in the storage 120 (Step 302). Once the proper forms-scanning document has been selected, field-specific dictionaries linked to the fields in that selected forms-scanning template are loaded (Step 304). Next, the intelligent analysis module 130 analyzes the converted text content from the filled-in form present in the individual fields, on a field by field basis using the field-specific dictionary linked to each respective field, for misspellings or improper entries, or for missing content (Step 306).

On a field by field basis, the intelligent analysis module 130 determines whether there is any misspelled or improper content in that field (Step 308). If there are no misspellings or improper content and more fields to process, the intelligent analysis module 130 will process the next field (Step 318). If there is any misspelled or improper content in that field, then the intelligent analysis module 130 will attempt to find the closest fit correction if a discrepancy between the misspelled or improper content is unlikely (Step 310). If a closest fit is found (Step 312), the intelligent analysis module 130 will automatically replace that content with its closest fit (Step 314) and, again, and if there are more fields to process, the intelligent analysis module 130 will process the next field (Step 318).

If a closest fit is not found (or where there is a likelihood of discrepancy between the content and two or more potential closest fit possibilities) (Step 312) then the error is flagged for operator correction (Step 316) and, again, if there are more fields to process, the intelligent analysis module 130 will process the next field (Step 318).

If all fields have been processed, if any errors have been flagged (Step 316), an indication of the errors are provided to the operator (Step 320). The intelligent analysis module 130 will then receive the operator's correction(s) (Step 322) and update the dictionar(y/ies) as appropriate based upon the correction(s) (Step 324).

Optionally, depending upon the particular implementation, the intelligent analysis module 130 can also create new associations based upon the operator correction(s) (Step 326) to enable it to avoid flagging a similar error in the future. Finally, the intelligent analysis module 130 will load the next document, if any, to process (Step 328) and repeat. Optionally, if all fields have been processed and there were no errors flagged (Step 316) for the entire document, as shown by the dashed arrow Step 320 through (optional) Step 326 can be bypassed, so that the next document to process, if any, will be loaded (Step 328).

Having described and illustrated the principles of this application by reference to one or more example embodiments, it should be apparent that the embodiment(s) may be modified in arrangement and detail without departing from the principles disclosed herein and that it is intended that the application be construed as including all such modifications and variations insofar as they come within the spirit and scope of the subject matter disclosed.

What is claimed is:
1. A forms processing system comprising:
   i) at least one processor;

ii) non-transitory storage coupled to the at least one processor;
iii) at least one of an intelligent character recognition (ICR) or intelligent word recognition (IWR) program stored in the storage and executable by the at least one processor;
iv) multiple selectable forms-scanning templates, stored in the storage and selectable for use with the at least one ICR or IWR program based upon an analysis of an individual form to be scanned for text conversion using the at least one ICR or IWR program, each of the multiple forms-scanning templates having multiple fields, defining specific content areas of filled-in forms to be scanned for graphic content that is to be recognized and converted into text content using the at least one ICR or IWR program;
v) an intelligent analysis module, stored within the storage and executable by the at least one processor which, when executed, will load field-specific dictionaries, based upon fields within a particular template, and analyze converted text content obtained from within the recognized specific content areas of a filled-in form for misspellings or improper entries using the field-specific dictionaries before saving the converted text content into the storage;
vi) a first field-specific dictionary, stored in the storage and linked to one of the fields of one of the forms-scanning templates, the first field-specific dictionary being used by the intelligent analysis module to check for misspelling or improper entry within first converted text content located within a first content area of a scanned filled-in form document, the first content area corresponding to the one of the fields, and having been converted by the at least one ICR or IWR program;
vii) a second field-specific dictionary, different from the first, stored in the storage, and linked to an other of the fields of the one forms-scanning template, the second field-specific dictionary being used by the intelligent analysis module to check for misspelling or improper entry within second converted text content located within a second content area of the scanned filled-in form document, the second content area corresponding to the other of the fields and having been converted by the at least one ICR or IWR program;
viii) wherein, the intelligent analysis module will, when analysis of particular content in one of the first field or the second field indicates that the particular content may be misspelled or improper or is absent from the respective first or second field-specific dictionary linked to the first field or the second field, and based upon which of the first or second fields contains the particular content that is misspelled or improper, will attempt to identify a closest fit between the particular content and contents of the respective first or second field-specific dictionary and either
   a) automatically replace the particular content with an entry from the respective first or second field-specific dictionary corresponding to the closest fit when a discrepancy between the particular content and the entry is not likely, or
   b) if there is no closest fit or the particular content is absent, provide an indication of an error to an operator, via a user interface, and allow the operator to provide a correction for the particular content; and
ix) wherein, if the correction provided by the operator does not correspond to content within the respective first or second field-specific dictionary, the intelligent analysis module will automatically store the correction as a new entry within the respective first or second field-specific dictionary in the storage for use by the intelligent analysis module in a subsequent analysis of new content from a new scanned form document involving the respective first or second field-specific dictionary to which the correction was added.

\* \* \* \* \*